United States Patent [19]

Dorn et al.

[11] 4,235,932
[45] Nov. 25, 1980

[54] PESTICIDAL 1,4-BIS-[(-PROPYNYLOXY)-METHYL]-BENZENE AND 1,4-BIS-[(2-PROPYNYLOXY)-METHYL] CYCLOHEXANE

[75] Inventors: Silvia Dorn, Dielsdorf; Albert Pfiffner; René Zurflüh, both of Bülach, all of Switzerland

[73] Assignee: Hoffmann-La Roche Inc., Nutley, N.J.

[21] Appl. No.: 43,204

[22] Filed: May 29, 1979

[30] Foreign Application Priority Data

May 31, 1978 [CH] Switzerland ............... 5957/78

[51] Int. Cl.³ ............................................. A01N 31/00
[52] U.S. Cl. ............................ 424/339; 424/DIG. 8; 568/654; 568/670
[58] Field of Search ................. 424/339, DIG. 8; 568/670, 654

[56] References Cited

U.S. PATENT DOCUMENTS 3,839,562 10/1974 Subraya et al. .................. 424/339
3,840,604 10/1974 Subraya et al. .................. 424/339

OTHER PUBLICATIONS

Bulletin of the Chemical Society of Japan 40, 363-370 (1967).

*Primary Examiner*—Allen J. Robinson
*Attorney, Agent, or Firm*—Jon S. Saxe; Bernard S. Leon; William M. Farley

[57] ABSTRACT

Compounds represented by the formula

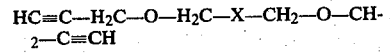

wherein X is phenylene or cyclohexylene as well as pesticidal compositions containing these compounds as the active ingredient, and methods for their use, are disclosed.

6 Claims, No Drawings

PESTICIDAL 1,4-BIS-[(-PROPYNYLOXY)-METHYL]-BENZENE AND 1,4-BIS-[(2-PROPYNYLOXY)-METHYL] CYCLOHEXANE

SUMMARY OF THE INVENTION

The pesticidal compositions of this invention contain inert carrier material and, as the active ingredient, a compound of the formula

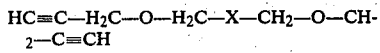

HC≡C—H$_2$C—O—H$_2$C—X—CH$_2$—O—CH$_2$—C≡CH    I,a wherein X is phenylene or cyclohexylene.

This invention is also directed to the novel compound-1,4-bis-[(2-propynyloxy)methyl]-cyclohexane.

Methods, utilizing the pesticidal compositions of this invention, for the control of pests are also disclosed.

DETAILED DESCRIPTION OF THE INVENTION

The active ingredient of the pesticidal compositions of this invention is a compound of the formula:

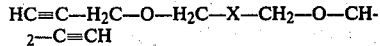

HC≡C—H$_2$C—O—H$_2$C—X—CH$_2$—O—CH$_2$—C≡CH    I,a wherein X is phenylene or cyclohexylene.

The novel compound of this invention, 1,4-bis-[(2-propynyloxy)-methyl]-cyclohexane, can be prepared by the following methods.

A. A compound of the formula

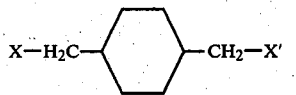

wherein X and X' each are chlorine, bromine, iodine, mesyloxy or tosyloxy,
is reacted with at least 2 moles of a compound of the formula

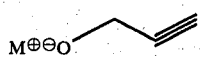

III wherein M⊕ is an alkali metal or alkaline earth metal ion.

The reaction of an alcoholate of formula III with a compound of formula II is carried out in an inert organic solvent, preferably dimethylformamide, dioxan, hexamethylphosphoric acid triamide, tetrahydrofuran, dimethoxyethane or a mixture of two or more of these solvents.

An alcoholate of formula III is prepared from the corresponding alcohol by admixing the alcohol with an alkali metal, alkaline earth metal, an alkali metal or alkaline earth metal hydride or amide or an alkali metal hydroxide. The preferred alkali metals are sodium and potassium while the preferred alkaline earth metals are calcium and magnesium.

In the reaction of an alcoholate of formula III with a compound of formula II, the reaction temperature is not critical and can range from 0°–20° C. up to the boiling point of the reaction mixture. A preferred reaction temperature is 50°–70° C., especially when X and X' in formula II each are bromine.

B. A compound of the formula

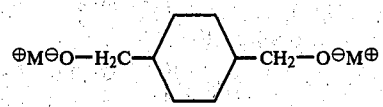

IV wherein M+ is an alkali metal or alkaline earth metal ion,
is reacted with a compound of the formula

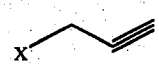

V wherein X is chlorine, bromine, iodine, mesyloxy or tosyloxy.

The reaction of the alcoholate of formula IV with a compound of formula V is carried out under the same conditions as described above in procedure A.

The preferred compound of formula I is alpha, alpha'-bis-(2-propynyloxy)-p-xylene,

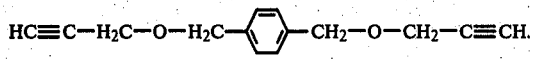

This compound is described in the Bulletin of the Chemical Society of Japan 40, 363–370(1967). The synthesis occurred as a result of a spectroscopic investigation.

The pesticidal compositions of this invention are prepared by mixing inert carrier material with a compound of formula I as the active ingredient.

The term "inert carrier material" includes carrier substances, wetting agents, inert diluents and solvents.

Since the compounds of formula I are, in general, water-insoluble, they can be prepared as ready-to-use compositions by any of the standard methods. For example, the compounds of formula I can be dissolved in a water-immiscible solvent such as, for example, a high-boiling hydrocarbon, which contains dissolved emulsifiers. The resulting solution acts as a self-emulsifiable oil upon addition to water.

The compounds of formula I can also be mixed with a wetting agent, with or without inert diluent, to form a wettable powder which is soluble or dispersible in water.

Wetting agents suitable for use in the pesticidal compositions of this invention can be anionic, cationic or non-ionic.

Examples of anionic wetting agents include soaps; fatty sulfate esters such as dodecyl sodium sulfate, octadecyl sodium sulfate and cetyl sodium sulfate; fatty-aromatic sulfonates such as alkylbenzenesulfonates or butylnaphthalenesulfonates; or complex fatty sulfonates such as amide condensation products of oleic acid and N-methyltaurine or the sodium sulfonate of dioctyl succinate.

Examples of cationic wetting agents include cetyl-trimethylammonium bromide and the like.

Examples of non-ionic wetting agents include condensation products of fatty acids, fatty alcohols or fat-substituted phenols with ethylene oxide; fatty acid esters and ethers of sugars or polyvalent alcohols; products obtained from condensation of fatty acid esters and ethers of sugars or polyvalent alcohols with ethylene oxide or block copolymers of ethylene oxide and propylene oxide.

The compounds of formula I can also be mixed with inert diluents to form solid or pulverous products.

Inert diluents with which the compounds of formula I can be processed comprise solid inert media including pulverous or finely divided solid substances such as clays, sands, talc, mica, fertilizers and the like. These inert diluents can be present either as dusts or as materials of larger particle size.

The pesticidal compositions of this invention can also be in the form of aerosols comprising a compound of formula I, a propellant gas, a co-solvent and a wetting agent. The propellant gas is suitably a polyhalogenated alkane such as dichlorodifluoromethane.

In addition to an active compound of formula I, the pesticidal compositions of this invention can contain active ingredients such as synergists, insecticides, bactericides and fungicides.

Application of a compound of formula I to plants, animals, soil, objects and other surfaces is effective in the control of pests.

The pesticidally effective amount of an active ingredient of formula I in a pesticidal composition of this invention can vary depending on the field of application. For example, in the treatment of plants for the control of pests thereon, from about 100 to about 2000 g/ha of active ingredient should be applied. In the treatment of animals for the control of ectoparasites thereon, the animal is either dipped in a solution containing 10–500 ppm of active ingredient or sprayed with such a solution.

The acute toxicity in mice of the compounds of formula I is above 1000 mg/kg.

The pesticidal compositions of this invention are especially valuable as insecticides and acaricides against Coleoptera such as Epilachna spp. and *Leptinotarsa decemlineata*; against Homoptera and especially against the family Aleyrodidae such as *Trialeurodes vaporariorum, Aleurodes proletella, Aleurothrixus floccosus, Dialeurodes citrifolii, Benisia tabaci* and *Aleurocanthus woglumi*; against species of other Homoptera families such as Planococcus spp. and Psylla spp.; against Lepidoptera such as *Spodoptera littoralis, Adoxophyes reticulana, Ostrinia nubilalis* and *Helrothis virescens* and moths and against Acarina such as *Tetranychus urticae, Panonychus ulmi* and tetrapodile mites.

The present invention is also concerned with a method for providing a locus subject to or subjected to attack by pests free from such attack, which method comprises applying to said locus an effective amount of a pesticidal composition as defined hereinabove.

The compounds of formula I are direct insecticides and acaricides and, to some extent, have systemic activity. A preferred aspect of the action of the compounds of formula I is their activity in the vapor phase. This is especially effective for the ovicidal action of these compounds.

The compounds of formula I,a can exist not only in cis/trans mixtures but also in the cis form or in the trans form.

The following Examples illustrate the invention.

In Examples 6–13 the following compounds were evaluated against a variety of pests.

| Active Ingredient | Structure | Name |
|---|---|---|
| A | | 1,4-Bis-[(2-propynyloxy)-methyl]-cyclohexane (cis/trans mixture) |
| B | | Alpha,alpha'-bis(2-propynyloxy)-p-xylene |
| Chlordimeform | Cl—C₆H₃(CH₃)—N=CH—N(CH₃)₂ | N'-(4-Chloro-2-methylphenyl)-N,N-dimethylformamidine |
| Zinophos | (C₂H₅O)₂P(=S)—O—(pyrazin-2-yl) | O,O-Diethyl-O-(pyrazin-2-yl)-monothiophosphate |

EXAMPLE 1

303.75 g of a 55% sodium hydride suspension were washed three times with 200 ml of hexane. 990 ml of absolute dimethylformamide were added to and covered the suspension. 502 g. of cis/trans 1,4-bis-(hydroxymethyl)-cyclohexane in 2000 ml of absolute dimethylformamide were added to the sodium hydride suspension over a one hour period at room temperature and under a nitrogen atmosphere. The mixture was stirred at 40° C. until the evolution of hydrogen ceased. The reaction mixture was cooled to room temperature and 910 g. of propargyl bromide were slowly added dropwise with the temperature rising to about 38° C. This mixture was stirred at 40° C. for 16 hours and then cooled to room temperature. 350 ml of acetic acid were added cautiously under a nitrogen atmosphere. The reaction mixture was then poured onto a ice/water mixture. The product was exhaustively extracted with methylene chloride, washed neutral with water, dried and evaporated. Fractional distillation yielded pure 1,4-bis-[(2-propynyloxy)-methyl]-cyclohexane; b.p. 116° C./0.05 Torr; m.p. 56°–60° C. (cis/trans mixture).

EXAMPLE 2

A pesticidal composition containing alpha, alpha'-bis-(2-propynyloxy)-p-xylene as the active ingredient and the following ingredients was prepared

| Ingredient | g/l |
|---|---|
| α,α'-bis-[(2-propynyloxy)]-p-xylene | 500.0 |
| Mixture of castor oil and ethylene oxide condensation product with ca 25 mol of ethylene oxide and calcium dodecylbenzenesulfonate in the ratio 3:1 | 100.0 |
| Epoxidized soya oil with an oxirane oxygen content of 6% | 25.0 |
| Butylated hydroxytoluene | 10.0 |
| Solvent consisting of a mixture of mono-, di- and tri(lower alkyl)-benzenes to | 1000 ml |

EXAMPLE 3

The following pesticidal composition containing 1,4-bis-[(2-propynyloxy)-methyl]-cyclohexane as the active ingredient was prepared

| Ingredient | g/100g |
|---|---|
| 1,4-Bis-[(2-propynyloxy)-methyl]-cyclohexane | 50.0 g |
| High-dispersible silicic acid | 5.0 g |
| Sodium laurylsulfate | 1.0 g |
| Sodium lignosulfonate | 2.0 g |
| Kaolin | 42.0 g |
| | 100.0 g |

EXAMPLE 4

The following pesticidal composition containing 1,4-bis-[(2-propynyloxy)-methyl]-cyclohexane as the active ingredient was prepared.

| Ingredient | g/l |
|---|---|
| 1,4-Bis-[(2-propynyloxy)-methyl]-cyclohexane | 250 |
| N-methyl-2-pyrrolidone | 300 |
| Mixture of castor oil and ethylene oxide condensation product with ca 25 mol of ethylene oxide and calcium dodecylbenzenesulfonate in the ratio 3:1 | 50 |
| Cycloalkylepoxystearate | 25 |
| Solvent consisting of a mixture of mono-, di- and tri(lower alkyl)-benzenes to | 1000 ml |

EXAMPLE 5

The following pesticidal composition containing 1,4-bis-[(2-propynyloxy)-methyl]-cyclohexane as the active ingredient was prepared.

| Ingredient | g/100g |
|---|---|
| 1,4-Bis-[2-propynyloxy)-methyl]-cyclohexane | 25.0 g |
| High-dispersible silicic acid | 5.0 g |
| Fossil silicic acid | 25.0 g |
| Sodium lauryl sulfate | 1.0 g |
| Sodium lignosulfonate | 2.0 g |
| Kaolin | 42.0 g |

-continued

| Ingredient | g/100g |
|---|---|
| | 100.0 g |

EXAMPLE 6

Bush beans infected with eggs of *Trialeurodes vaporariorum* (white fly) were treated with aqueous spray liquors of an active ingredient. Seven days after treatment, the hatching rate were determined. The results are reported in Table 1 as the percent reduction of the hatching rate in comparison to untreated controls. (Untreated Control egg mortality is 8%).

TABLE 1

| Formulation | Active Ingredient | % Active Ingredient | % Reduction |
|---|---|---|---|
| Example 4 | A | 0.1 | 100 |
| | | 0.03 | 100 |
| | | 0.01 | 100 |
| | | 0.003 | 44 |
| | | 0.001 | 7 |
| Example 3 | A | 0.1 | 100 |
| | | 0.03 | 100 |
| | | 0.01 | 100 |
| | | 0.003 | 89 |
| | | 0.001 | 20 |
| Example 2 | B | 0.1 | 100 |
| | | 0.03 | 100 |
| | | 0.01 | 100 |
| | | 0.003 | 75 |
| | | 0.001 | 45 |
| — | Zinophos (Nemaphos) | 0.1 | 0 |
| | | 0.03 | 0 |
| | | 0.01 | 0 |
| | | 0.003 | 0 |
| | | 0.001 | 0 |

Nemaphos (Zinophos) is a commercial forulation obtained from Dr. R. Maag AG.

EXAMPLE 7

Brussel sprouts with a large population of *Aleurodes proletella* (white fly) were sprayed with an aqueous spray liquor of the active ingredient. After 4 weeks, young larvae were again counted. The results are reported in Table 2 as the percentage reduction of the population (ovolarvicidal activity) in comparison with the untreated controls. (Untreated controls had a population of 486 larvae.

TABLE 2

| Formulation | Active Ingredient | % Active Ingredient | % Reduction |
|---|---|---|---|
| Example 5 | A | 0.1 | 98 |
| | | 0.05 | 90 |
| | | 0.025 | 97 |
| Example 2 | B | 0.1 | 100 |
| | | 0.05 | 96 |
| | | 0.025 | 97 |
| — | Zinophos NEMAPHOS | 0.1 | 0 |
| | | 0.05 | 0 |
| | | 0.025 | 0 |

EXAMPLE 8

Pumpkin plants with freshly laid *Epilachna chrysomelina* (cucumber beetle) eggs were sprayed with an aqueous spray liquor of active ingredient. After 6 days, the hatching rate was determined. The results are reported in Table 3 as the percentage reduction of the hatching rate in comparison with the untreated controls. (untreated Control egg mortality is 8%).

TABLE 3

| Formulation | Active Ingredient | Active Ingredient | % Reduction |
|---|---|---|---|
| Example 3 | A | 0.1 | 100 |
| | | 0.03 | 100 |
| | | 0.01 | 93 |
| | | 0.003 | 61 |
| | | 0.001 | 13 |
| Example 4 | A | 0.1 | 100 |
| | | 0.03 | 57 |
| | | 0.01 | 3 |
| | | 0.003 | 0 |
| | | 0.001 | 0 |
| Example 2 | B | 0.1 | 100 |
| | | 0.03 | 94 |
| | | 0.01 | 55 |
| | | 0.003 | 3 |
| | | 0.001 | 4 |
| — | Chlordimeform GALECRON | 0.1 | 0 |
| | | 0.03 | 0 |
| | | 0.01 | 0 |
| | | 0.003 | 0 |
| | | 0.001 | 0 |

Galecron (chlordimeform) is a commercial formulation obtained from Ciba-Geigy.

EXAMPLE 9

Lids of Petri dishes were treated with an aqueous spray liquor of the active ingredient. After drying of the spray layer, an egg-laying *Epilachna chrysmelina* (cucumber beetle) was placed in the bottom of the Petri dish. The dish was closed with the treated cover. After 6 days, the hatching rate was determined. The results, reported in Table 4 below, are expressed as percent reduction of the hatching rate in comparison with the untreated controls. (Untreated Control egg mortality is 7%).

TABLE 4

| Formulation | Active Ingredient | % Active Ingredient | % Reduction |
|---|---|---|---|
| Example 4 | A | 0.1 | 100 |
| | | 0.03 | 44 |
| | | 0.01 | 0 |
| | | 0.003 | 0 |
| | | 0.001 | 0 |
| Example 2 | B | 0.1 | 100 |
| | | 0.03 | 100 |
| | | 0.01 | 88 |
| | | 0.003 | 65 |
| | | 0.001 | 13 |
| — | Chlordimeform GALECRON | 0.1 | 0 |
| | | 0.03 | 0 |
| | | 0.01 | 0 |
| | | 0.003 | 0 |
| | | 0.001 | 0 |

EXAMPLE 10

Maize plants with freshly laid *Ostrinia nubilalis* (European corn borer) eggs were sprayed with an aqueous spray liquor of the active ingredient. After 6 days, the hatching rate was determined. The results, reported in Table 5 below, are expressed as percent reduction of the hatching rate in comparison with the untreated controls. (Untreated control egg mortality is 7%).

TABLE 5

| Formulation | Active Ingredient | % Active Ingredient | % Reduction |
|---|---|---|---|
| Example 4 | A | 0.1 | 52 |
| | | 0.01 | 0 |
| Example 2 | B | 0.1 | 100 |
| | | 0.01 | 37 |
| — | Chlordimeform GALECRON | 0.1 | 28 |
| | | 0.01 | 7 |

EXAMPLE 11

Potato plants with freshly laid *Leptinotarsa decemlineata*, (Colorado potato beetle) eggs were sprayed with an aqueous spray liquor of the active ingredient. After 6 days, the hatching rate was determined. The results, reported in Table 6, are expressed as percent reduction of the hatching rate in comparison with the untreated controls. (Untreated control egg mortality is 1%).

TABLE 6

| Formulation | Active Ingredient | % Active Ingredient | % Reduction |
|---|---|---|---|
| Example 3 | A | 0.1 | 86 |
| | | 0.03 | 0 |
| | | 0.01 | 0 |
| Example 2 | B | 0.1 | 100 |
| | | 0.03 | 41 |
| | | 0.01 | 0 |
| — | Chlordimeform GALECRON | 0.1 | 87 |

EXAMPLE 12

Lids of Petri dishes were treated with an aqueous spray liquor of active ingredient. After the drying of the spray layer, an egg-laying *Leptinotarsa decemlineata* (Colorado potato beetle) was placed in the bottom of the Petri dish. The dish was closed with the treated lid. After 6 days, the hatching rate was determined. The results, reported below in Table 7, are expressed as percent reduction of the hatching rate in comparison with the untreated controls. (Untreated control egg mortality is 1%).

TABLE 7

| Formulation | Active Ingredient | % Active Ingredient | % Reduction |
|---|---|---|---|
| Example 4 | A | 0.1 | 100 |
| | | 0.03 | 0 |
| | | 0.01 | 0 |
| | | 0.003 | 0 |
| | | 0.001 | 0 |
| Example 2 | B | 0.1 | 100 |
| | | 0.03 | 100 |
| | | 0.01 | 79 |
| | | 0.003 | 19 |
| | | 0.001 | 49 |
| — | Chlordimeform GALECRON | 0.1 | 83 |
| | | 0.03 | 19 |
| | | 0.01 | 1 |
| | | 0.003 | 0 |
| | | 0.001 | 0 |

EXAMPLE 13

Petri dish lids were treated with an aqueous spray liquor of active ingredient and placed in the bottom of a desiccator. The desiccators were then closed. In various time intervals after the treatment, egg-layings of Spodoptera littoralis (cotton moth) are suspended in the desiccators and exposed to the active ingredient atmosphere for 6 hours. After 6 days, the hatching rate was determined. The results, reported below in Table 8, are expressed as percent reduction of the hatching rate in comparison with the untreated controls. (The untreated control egg mortality is 2% after 14 days, 3% after 22 days, after 35 and 49 days and 2% after 56 days.)

TABLE 8

| Formulation | Active Ingredient | mg. Active Ingredient/m$^3$ | % Reduction after | | | | | |
|---|---|---|---|---|---|---|---|---|
| | | | 0 | 14 | 22 | 35 | 49 | 56 days |
| Example 2 | B | .150 | 100 | 100 | 100 | 100 | 100 | 53 |
| — | Chlordimeform GALECRON | .150 | 100 | 59 | 30 | 0 | 0 | 0 |

We claim:

1. An insecticical and acaricidal composition which comprises inert carrier material and, as the active ingredient, an amount which is effective as an insecticide and acaricide, of a compound of the formula $$HC\equiv C-CH_2-O-CH_2-X-CH_2-O-CH_2-C\equiv CH$$

wherein X is

[cyclohexane ring structure]

2. A method for the control of insects and acarids which comprises treating the insects and acarids with a insecticidally and acaricidally effective amount of the composition of claim 1.

3. A method for providing a locus subject to or subjected to attack by insects and acarids free from such attack which comprises applying to said locus a insecticidal and acaricidal effective amount of the composition of claim 1.

4. An insecticidal and acaricidal composition which comprises solid inert pesticide carrier material and, as the active ingredient, an amount which is effective as an insecticide and acaricide, of a compound of the formula $$HC\equiv C-CH_2-O-CH_2-X-CH_2-O-CH_2-C\equiv CH$$

wherein X is

[benzene ring structure]

5. A method for the control of insects and acarids which comprises treating the insects and acarids with a insecticidally and acaricidally effective amount of the composition of claim 4.

6. A method for providing a locus subject to or subjected to attack by insects and acarids free from such attack which comprises applying to said locus a insecticidal and acaricidal effective amount of the composition of claim 4.

* * * * *